United States Patent [19]

Bergmann

[11] Patent Number: 5,721,105
[45] Date of Patent: Feb. 24, 1998

[54] METHOD FOR THE IMMUNOLOGICAL DETERMINATION OF PROTEINS AND KIT FOR CARRYING OUT THE METHOD

[75] Inventor: Andreas Bergmann, Berlin, Germany

[73] Assignee: B.R.A.H.M.S. Diagnostica GmbH, Germany

[21] Appl. No.: 529,880

[22] Filed: Sep. 18, 1995

Related U.S. Application Data

[63] Continuation-in-part of Ser. No. 517,278, Aug. 21, 1995, abandoned.

[30] Foreign Application Priority Data

Feb. 20, 1994 [DE] Germany .................. 195 05 732.5
Aug. 19, 1994 [DE] Germany .................. 44 29 409.3

[51] Int. Cl.$^6$ .................... G01N 33/53; A61K 35/14
[52] U.S. Cl. ................. 435/7.1; 435/4; 435/7.2; 435/7.24; 530/380
[58] Field of Search ................. 435/4, 7.1, 7.2, 435/7.24; 530/380

[56] References Cited

PUBLICATIONS

"Enzymun–Test Systeme", Firmenschrift, Boehringer Mannheim GmbH, 1990, S.22 u. 23.
Schlumberger et al, "A New Immunoradiometric Assay (IRMA) System for Thyroglobulin Measurement in the Follow–up of Thyroid Cancer Patients," European Journal of Nuclear Medicine 18 (1991), 153–157.
Heinze et al, "Spectrum of Serum Thyroglobulin Elevation in Congenital Thyroid Disorders", Thyroid, vol. 3, No. 1, 1993, 37–40.
"Dynotest Tg", Arbeitsanleitung, Henning Berlin GmbH, Berlin, Jul. 1992.
"Thyroglubuline IRMA Pasteur", Code 79831, E.R.J.A. Diagnostics Pasteur, Marnes La Cognette, Franreich, Jan. 1991, 1–34.
R. Sapin et al, "Recovery Determination in 600 Sera Analyzed for Thyroglobulin With a Recently Commercialized IRMA Kit", Clin. Chem. 38 (1992) 9, 1920–1921.
"Synchron Enzyme Linked Immuno Sorbent Assay", Elias Medizintechnik GmbH. Freiburg, Feb. 1990.
"DYNOTEST® Tg", second preliminary report on a collaborative study with contributions, Henning Berlin GmbH, pp. 2–56 + Contents and back page.

Dienstauflage der kassenartztlichen Bundesvereinigung. "Einheitlicher Bewertungsmassstab (EBM)", Stand 01.01.94, Deutscher Arzte Verlag. S. 214, Pos. 4152.
Chemical Abstracts, vol. 120, 1994 40426d Kasagi "Fundamental and clinical evaluation of an immunoradiometric assay for thyroglobulin in sera with positive autoantibodies".
Kasagi et al, "Fundamental and clinical evaluation of an immunoradiometric Assay for Thyroglobulin in Sera with Positive Autoantibodies", Department of Radiology, Faculty of Medicine, Kyoto University, (1993) (corresponds to Chemical Abstracts vol. 120: p. 481, No. 49426d.
Chemical Abstracts, vol. 120, 1994 26488m.
Sato, et al, "Measurement of Thyroglobulin in blood by immunoradiometric assay", vol. 13, No. 4 (1993) (corresponds to Chemical Abstracts vol. 120, 1994 26488m).
Chemical Abstracts, vol. 102, 1985 109105p Van Herle, "An International cooperative study evaluating serum thyroglobulin standards."
Van Herle et al, "An International Cooperative Study Evaluating Serum Thyroglobulin Standards", Journal of Clinical Endocrinology and Metabolism, vol. 60, No. 2, pp. 338–343 (corresponds to Chemical Abstracts vol. 102: p. 339, No. 109105p).
Nakamura et al, Handbook of Exp. Immunol, 4th Ed, 1986 p. 27.5.

*Primary Examiner*—Lila Feisee
*Assistant Examiner*—Susan Ungar
*Attorney, Agent, or Firm*—Cushman Darby & Cushman IP Group of Pillsbury Madison & Sutro, LLP

[57] ABSTRACT

A method for the immunological determination of proteins or polypeptides which are suitable as tumour tracers, in particular human thyroglobulin, in a sample of a biological fluid. The method comprises placing a sample of the fluid to be tested in solution with immunological binding partners for the protein or polypeptide to be determined and obtaining a signal representative of the amount of the protein or polypeptide, wherein a fixed known amount of the protein or polypeptide to be measured is added to each test sample and to the standards for the calibration curve before the measurement is made. If the signal obtained for the unknown sample is stronger than the signal obtained for the zero standard, the result is considered a positive measured value which is indicative of the presence and amount of the protein or polypeptide in the sample, and if it is weaker the result is considered an indication of a systematic bias of the measured value.

12 Claims, 3 Drawing Sheets

Method according to the invention Tg [ng/ml]

METHOD FOR THE IMMUNOLOGICAL DETERMINATION OF PROTEINS AND KIT FOR CARRYING OUT THE METHOD

This is a Continuation-in-Part of application Ser. No. 08/517,278, filed Aug. 21, 1995, which is abandoned.

BACKGROUND OF THE INVENTION

1. Field of the Invention

The present invention relates to a method for the immunological determination of proteins or polypeptides which are suitable as tumour tracers in a sample of a biological fluid by reacting them with immunological binding partners for the protein or polypeptide to be determined, in a measuring solution, and obtaining a result which is evaluated using standard curves prepared with the aid of standard samples and a zero standard, further components of a protein or peptide nature, which lead to systematic falsification of the measured values, being likely to be present in the biological fluid.

2. Background Information

In clinical diagnostics, the detection and the quantitative determination of proteins and polypeptides, the occurrence of which in body fluids of patients is an indication of the existence of various types of tumour tissue in the body of a patient and which are therefore known as tumour tracers, are of considerable importance. Examples of tumour tracers of this type in the context in which this term is used in the present application are—using the usual abbreviations—the prostate-specific antigen (PSA), the carcino-embryonal antigen (CEA), the tumour antigens CA 19-9, CA 1-5, CA 72-4 and CA 15-3, alphafetoprotein (AFP), PAP and other tumour antigens of a protein or a polypeptide nature which are known to a person skilled in the art, and in particular the protein thyroglobulin, which will be discussed in particular below and for the determination of which the present invention is of particular importance. The present invention is therefore illustrated in detail primarily with reference to the determination of human thyroglobulin. The determination of the proteins and polypeptides serving as tumour tracers is carried out in clinical diagnostics primarily with the use of immunological assay methods or immunoassays, the essential characteristic of which is that selective binding reactions of the tumour tracers acting as antigens with their immunological binding partners are utilized. Many different basic methods for the immunological determination of proteins and polypeptides or antigens generally are now known to a person skilled in the art, some of which, such as the classical RIA, are based on a competition principle where, for example, the substance to be determined and a known amount of the same substance which has been labelled compete for a limited number of binding sites of an immunological binding partner, for example of an antibody, or constitute the so-called immunometric determinations, in which labelled binding partners are used. The most well known version of the so-called immunometric determination is the classical "sandwich assay", in which the substance to be determined is extracted from the sample by means of an excess of a first immunological binding partner and is bound to a solid phase, after which the total extracted amount of the substance to be determined is labelled by reaction with another labelled binding partner which binds to another epitope of the substance to be determined.

A person skilled in the art is familiar with many classes of substance and reaction systems which are suitable for labelling, including radioactive isotopes, enzymes or substrates of an enzymatic reaction, or substances which serve as tracers owing to their fluorescence or their contribution to the chemiluminescence reaction. In the present invention, the choice of a suitable known tracer is not critical, and the present invention covers in principle all known tracers or tracers which may be found.

In the immunological determination of substances of a protein or polypeptide nature by reaction with suitable immunological binding partners, it is necessary for the immunological binding reaction on which the particular assay method is based and which takes place between the specific binding partners to be reproducible, in order to obtain an informative measured value. There are however cases where it is known that the immunological binding reaction on which an assay method is based can be disturbed if the serum or other body fluids of individual patients contain components which interfere with the immunological assay reaction. Examples of such components are reactive proteins and polypeptides which bind similarly to the substance to be determined to some partner of the particular immunological binding reaction and thus prevent it from entering into the immunological binding reaction on which the particular assay method is based. For example, in addition to the proteins or polypeptides to be determined, such patients may also have autoantibodies against the same protein or polypeptides, which, as a result of their binding, completely or partially prevent the actual binding reaction.

Other possible components which may falsify the measurement are foreign proteins or fragments of the protein to be determined which react with one of the binding partners, for example an antibody intended for the test, and thus likewise interfere with the determination. The presence of such further components manifests itself in a systematic falsification of the measured value, which results in no measured value or in too low a measured value being obtained, so that no reliable conclusions can be drawn on the basis of the measured value obtained.

It is therefore important clearly to recognize systematic falsifications of measured values which are caused by components present in the sample, this being achieved by an additional so-called recovery measurement. In the recovery measurement, a small, known amount of the substance to be determined is added to a further sample of the same measured biological fluid, and the measurement is repeated. If the assay method used gives correct values for the measured patient sample, the amount of the substance to be determined which was added to the recovery sample must appear in the recovery measurement as a corresponding increase in the measured value found beforehand in the first sample. As a rule, results within a certain standardized range about the region of a 100% recovery are regarded as positive results which can be used for a diagnosis. Since an incorrect diagnosis based on a single determination which was not checked by a recovery measurement may have serious consequences, the performance of a recovery measurement is prescribed for the immunological determination of many substances, in particular of tumour tracers. This is also evident from the fact that such tests which have to be carried out with a recovery measurement or confirmation measurement are subject to higher charges which are several times those for simple immunological investigations (cf., for example in Germany, the "Vertragsgebührenordnung der Kassenärztlichen Bundesvereinigung [Contractual Charge Regulation of the Panel Doctors' Federal Association]" (EPM), Item 4125 "human thyroglobulin with confirmation test").

The performance of a second recovery measurement or confirmation measurement gives rise to a number of disadvantages. On the one hand, the necessity of performing the recovery measurement or confirmation measurement makes a diagnosis considerably more expensive; on the other hand, it is constantly observed in practice that, contrary to the regulation, the recovery measurement or confirmation measurement is omitted, so that there is a danger that the doctor may incorrectly interpret the measured result obtained. Furthermore, a recovery measurement is carried out in such a way that the volume of an original patient sample which is measured is exactly identical to the volume measured in the original measurement, but that, owing to the known amount of the substance added in the form of a solution, the measurement is carried out in a slightly larger fluid volume than the original measurement. However, two separate measurements have been regarded as unavoidable to date, and the above-mentioned disadvantages were accepted.

SUMMARY OF THE INVENTION

It is the object of the present invention to design a method of the generic type, i.e. a method for the immunological determination of proteins or polypeptides which are suitable as tumour tracers in a sample of a biological fluid by their reaction with immunological binding partners for the protein or polypeptide to be determined, in a measuring solution, and obtaining a measured result which is evaluated using standard curves which are prepared with the aid of standard samples and of a zero standard, further components of a protein or peptide nature, which lead to a systematic falsification of the measured values, being likely to be present in the biological fluid, in such a way that it is possible to determine directly in the original measurement whether the determination performed is associated with a systematic falsification of the measured value.

According to the invention, this object is achieved if, in a method of the generic type, both the determination of proteins or polypeptides in the sample and the preparation of the standard curves are carried out with the aid of the standard samples and of a zero standard in the presence of a fixed amount of the protein or polypeptide to be determined, which is added to the measuring solution from the outset, and if the evaluation is carried out in such a way that a measured value which is obtained for a sample and is above the measured value obtained for the zero standard is regarded as a positive measured value which indicates the presence and concentration of the protein or polypeptide to be determined, while a measured value which is obtained for a sample and is below the measured value for the zero standard is regarded as an indication of a systematic falsification of the measured value.

Preferably, the method according to the invention is performed in such a way that the determination is carried out in a special sample vessel into which the added amount of the protein or polypeptide has already been introduced. The sample vessel is preferably a coated tube (CT) or a coated microtitre plate, which furthermore contains an immobilized immunological binding partner, for example an antibody, for the protein or polypeptide to be determined.

However, the known amount to be added can of course also be added in another manner, for example as an addition to other components of the kit which are added in specified proportions both to the standards and to the samples, for example as an addition to the tracer solution.

The known added amount of the protein or polypeptide is preferably chosen so that it gives a significant base value (measured value for the zero standard), which, according to experience, is ensured when the added amount of the protein or polypeptide in the measurement is in the range of 5 to 10 times the amount for the lower detection limit of the protein or polypeptide in the particular special immunological assay method.

An embodiment of the process according to the invention which is of particular interest to the Applicant relates to the immunological determination of human thyroglobulin. Thyroglobulin is a high molecular weight protein in which the thyroid hormone synthesis takes place and is at the same time the main component of the thyroid colloid. Without thyroglobulin itself having a direct physiological action, its presence and its quantity in the serum are an indication of the activity, in particular growth activity, of thyroid cells. In healthy people, the thyroglobulin content is in the range of about 10–50 ng Tg/ml. If a rapidly growing thyroid carcinoma is present, the thyroglobulin level in the serum is dramatically increased. However, the determination of thyroglobulin in connection with observation of the success of the surgical removal of a thyroid carcinoma is of particular importance since carcinoma cells which have not been removed and cells of the carcinoma tissue which are present as metastases produce thyroglobulin, which is detectable in the patient's serum. Thus, after total removal of the thyroid, the thyroglobulin value should decrease to 0 ng Tg/ml. If thyroglobulin is still detectable, this means that the body still contains thyroid tissue, possibly in the form of metastases of the carcinoma.

In the determination of human thyroglobulin, a recovery measurement has therefore been essential to date because a significant percentage of patients also exhibit components which lead to a systematic error of the type described above, in the form of a reduction in the measured value of the actual concentration of the substance to be determined in the sample. Such components are in particular anti-Tg autoantibodies, but it may be assumed that the samples also contain other components which interfere with the determination, since correspondence between the results of the recovery measurement and a direct determination of the amount of anti-Tg autoantibodies is not always found. For example, protein or polypeptide fragments of thyroglobulin are under discussion as other components of this type.

Where thyroglobulin is referred to predominantly as a tumour tracer in the present description of the invention, this does not imply any restriction of the method according to the invention to any specific purpose with regard to measurement; instead, every determination of thyroglobulin by a method which has the essential features according to the invention is covered by the present invention. The same applies to the measurement of other tumour tracers if they are also used for purposes other than the detection of a tumour.

According to the present invention, it has surprisingly been found that the recovery measurement can be dispensed with in the determination of human thyroglobulin (hTg), without significant loss of accuracy in the measurement, if all determinations and also the preparation of the standard curves are carried out in the presence of a fixed added amount of human thyroglobulin taken at the outset, i.e. under conditions where the measured value for the base signal for hTg is artificially increased. It has been found that an initially taken amount of thyroglobulin has no effect on the accuracy of the determination of the thyroglobulin concentration in the sample investigated if the determination does not involve any systematic falsification of the measured value, so that the assay method in such a case is just as exact as the method used to date for the original determination.

However, if the biological sample contains substances which interfere with the immunological assay method by, for example, preventing the correct formation of the sandwich in an immunometric assay method based on the sandwich principle, this manifests itself in the method according to the invention when the sample contains no thyroglobulin originating from the patient in any case as the determination of an excessively low measured value for the added amount of thyroglobulin, i.e. as a measured value which is below that for the zero standard.

If the patient's sample simultaneously contains both thyroglobulin and components which lead to a systematic falsification of the measured value, both effects overlap. However, the measured value obtained in the determination is as a rule nevertheless of higher clinical value: if the value obtained is lower than the measured value expected for the added amount, this is a reliable indication of a systematic falsification of the measured value, and the corresponding value should be discarded or checked by another method. If the amount of thyroglobulin determined is above the expected amount (in healthy people 10–90 ng Tg/ml, after total removal 0 ng Tg/ml), this is in any case an indication of an elevated thyroglobulin level in the serum investigated, so that in any case at least a qualitative conclusion can be drawn and if necessary further investigations can be requested.

The method according to the invention has an advantage whenever a recovery measurement has been omitted, since the danger of regarding an incorrect measured value as correct is greatly reduced by the clear detectability of systematic errors in the original measurement. Furthermore, in cases of doubt, the method according to the invention can be carried out in a simple manner as a confirmation measurement. In this case, the test is simply repeated using a different dilution of the patient's sample, the same test volume being employed. Since the ratio of the fixed added amount to the components of the patient's sample changes as a result of the dilution of the patient's sample, any previously masked measured value at the other dilution is detectable as a deviation from the expected value for the added amount. In this case, too, the method has the additional advantage that the same sample volumes can be used, i.e. a possible effect on the measured value by the increased volumes of the measuring solutions in the previous recovery measurements can be avoided.

The method according to the invention furthermore has the considerable practical advantage that it can be performed in a fully automated manner on conventional fully automatic machines for carrying out immunological assays, for which the recovery measurements required to date constituted an insoluble problem. In such a case, it is not essential to use test tubes which contain the added amount in lyophilized form as a wall coating; instead, it is then also possible to introduce the fixed added amount in the form of a solution into all test tubes by means of the automatic machine.

As shown by the following example of use, the method according to the invention proves in practice to be even more accurate in specific cases than the conventional assay method to be carried out with a recovery measurement, in that it permits a reliable distinction between correct and incorrect measured values in the grey zone where there is doubt about the correctness of a result obtained.

The feasibility and reliability of the method according to the invention was investigated in comparison with a commercial assay of the Applicant, which is sold as DYNOtest® Tg (placing a sample in a reaction vessel; reacting the sample with immunoglobulin binding partners for human thyroglobulin; obtaining a signal representing the amount of thyroglobulin in the sample, and evaluating the obtained signal using standard curves which are prepared with the aid of a series of standard samples containing known amounts of thyroglobulin including a zero standard sample which is thyroglobulin-free [DYNOTEST TG ASSAY]), the method according to the invention being an embodiment of the stated assay and directly based on it.

BRIEF DESCRIPTION OF THE DRAWINGS

By way of explanation reference is made to two tables and three figures with graphs, which show the following.

DETAILED DESCRIPTION OF THE INVENTION

Figure 1:
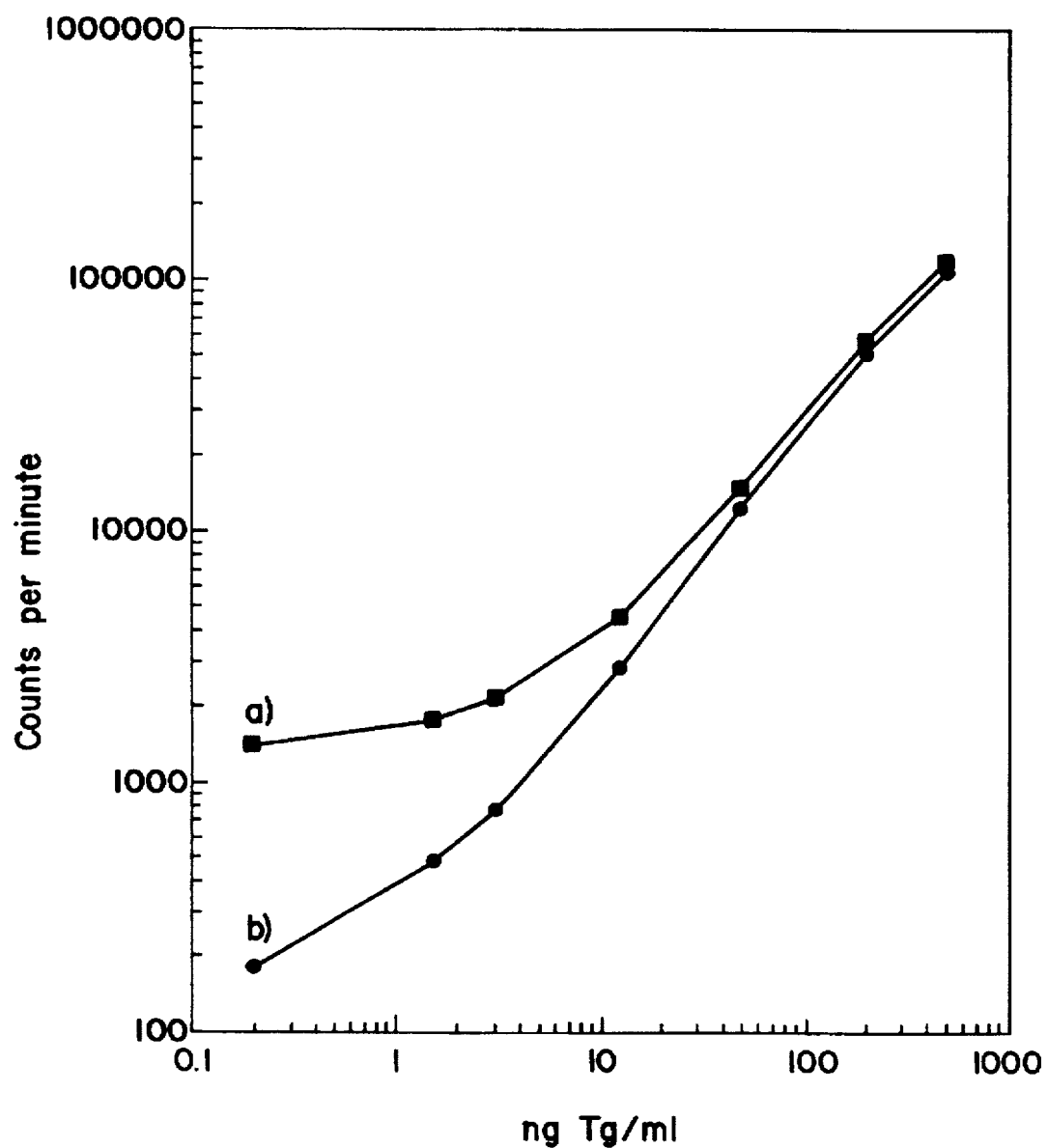
FIG. 1 shows typical standard curves for the determination of hTg by the known test (b) and by the method according to the invention (a)

The known DYNOTEST TG ASSAY is an immunoradiometric assay for the determination of thyroglobulin (Tg) in human serum. Two antigen-specific monoclonal antibodies recognizing different binding sites on the antigen (hTg) are used in excess. One of the two antibodies is radiolabelled (tracer) and the other is immobilized on the inner surface of the tube (coated tube technique).

During the incubation of the sample with the assay reagents, both antibodies react in succession with the hTg molecules of the sample to form a sandwich-type complex bound to the tube surface. After the end of the reaction, the remaining excess of tracer in the liquid phase is removed by aspirating or decanting and is discarded.

After washing twice, the radioactivity of the tubes is measured. The radioactivity is directly proportional to the hTg concentration of the respective sample in the absence of interfering components. Using standards added to the assay and a zero standard, a standard curve is prepared, from which the concentration of the hTg in the patient sera is determined by means of the radioactivities measured for the individual samples of the patient sera.

An assay of the stated type is sold as a kit (set of reagents) which contains the following components in amounts sufficient for 100 (2×50 determinations):

1. $^{125}$I-anti-hTg antibody (monoclonal; mouse) as radioactive tracer in two vials containing 10.5 ml each, ready for use, activity approx. 225 kBq per vial (at 70% counting efficiency), corresponding to approx. 80,000 cpm/200 μl
2. Coated tubes coated with anti-hTg antibody (monoclonal; mouse); 2×50 tubes; ready for use
3. 1 vial containing 3 ml of human serum as hTg zero standard, ready for use; defined as 0.2 ng Tg/ml. The zero standard is also intended to be used as a diluent for serum samples if relatively high hTg concentrations are expected.
4. hTg standards (human serum), 6 vials containing 0.4 ml each; ready for use; concentration: 1.6; 3.1; 12.5; 50; 200; 500 ng Tg/ml
5. Tg recovery sample, 1 vial containing 0.7 ml; ready for use; concentration: 500 ng Tg/ml. 10 μl thereof are pipetted into the measuring solution per recovery measurement.

6. Washing solution in two vials containing 10 ml each, as a concentrate which is to be diluted before use to 500 ml with distilled water in each case.
7. Three control sera I, II and III (human serum) in 3 vials containing 0.4 ml each; ready for use.

Test procedure:

In a test, 50 µl of Tg standard are pipetted into the labelled test tubes, and 50 µl of each serum sample are pipetted into the tubes for the samples.

A parallel recovery test is required for the zero standard and the serum samples, and 10 µl of recovery sample are added to a further set of test tubes containing 50 µl of serum sample. 10 µl of recovery sample are also added to a tube containing 50 µl of zero standard.

200 µl of tracer are then pipetted into each test tube and, after incubation overnight at room temperature, washing solution is added to the test tubes and the liquid is decanted or aspirated, washing being repeated twice.

The radioactivity of each tube is then measured in a gamma counter.

A standard curve is obtained from the measurements of the six standard samples, and the measured value for the serum samples is evaluated with reference to the stated standard curve. A typical standard curve for the known DYNOTEST TG ASSAY is shown as curve b) in FIG. 1.

The purpose of the prescribed recovery test is to discover systematic falsifications of the measured value. In the case of normal recovery, i.e. if the serum sample contains no factors which falsify the hTg determination, the hTg value in the recovery test must be about 100 ng/ml (corresponding to the added recovery sample) higher than the hTg value of the original serum sample determined in parallel.

The recovery is calculated according to the following formula $$\frac{\text{ng Tg/ml (W)} - \text{ng Tg/ml (Sample)}}{100 \text{ ng Tg/ml}} \times 100 = \% \text{ recovery}$$

In the above equation, (W) represents the measured result for a serum sample with the addition of the recovery sample and (Sample) represents the measured value of an original sample.

In the method, checking of the systematic reliability of the recovery determination procedure is also recommended. For this purpose, an additional recovery test is carried out for the zero standard and must give approx. 100 ng Tg/ml, corresponding to 100% recovery.

The tolerance range for the correct recovery is from 70 to 130% or 80 to 120%.

In the DYNOTEST TG ASSAY assay, a lower detection limit of <1 ng Tg/ml is obtained as the sensitivity of the assay.

Method According to the Invention

In order to carry out and check the method according to the invention, the kit (set of reagents) and the measurement protocol of the above DYNOTEST TG ASSAY was modified in such a way that a solution of 0.3 ng of hTg in 100 µl of phosphate-buffered saline solution (PBS) containing 1% of bovine serum albumin (BSA) was pipetted into all test tubes which had already been coated with the monoclonal anti-hTg antibody. By subsequent lyophilization, the amount of hTg introduced into the test tubes was transferred to the coat on the test tube walls.

Instead of using the tubes coated with hTg, however, it is within the scope of the present invention to add the fixed amount of another test component to be used in the case of each individual determination in essentially identical form, in particular to the tracer solution.

A reagent kit for carrying out the method according to the invention does not comprise a separate Tg recovery sample in any of the stated cases.

In a parallel test based on the method according to the invention, a standard curve (curve a) in FIG. 1) which corresponded to that for the commercial DYNOTEST TG ASSAY was prepared in the usual manner but in the presence of the added amount of hTg, and both standard curves were used for the evaluation of 179 serum samples, each of which was measured in the two assay systems.

Table 1 below shows the data for the preparation of the two standard curves a) and b) in FIG. 1, in cpm (counts per minute).

TABLE 1

|  | Concentration in ng Tg/ml | cpm a) | cpm b) |
|---|---|---|---|
| Hour 0 | 0 | 1410 | 181 |
| Hour 1 | 1.563 | 1754 | 477 |
| Hour 2 | 3.125 | 2147 | 770 |
| Hour 3 | 12.5 | 4543 | 2819 |
| Hour 4 | 50 | 15049 | 12621 |
| Hour 5 | 200 | 57698 | 51645 |
| Hour 6 | 500 | 123615 | 112313 |

Table 2 shows the results obtained, the first column showing the random patient's code, the second column showing the measured value obtained by the method according to the invention, the third column showing the measured value obtained by the known method and the fourth column showing the calculated recovery for the known method.

The results obtained by evaluating the original measured signals are stated as ng/ml, with the exception of those cases in which, in the test according to the invention, the occurrence of a systematic falsification of the measured value was detected on the basis of a decrease in the measured value for the added amount of Tg. In these cases, the result is expressed as a percentage of the base value expected for the added amount.

Two classes of serum samples are recognizable in Table 2, namely those in which, in the known test, the correctness of the sample measurement was confirmed in the recovery test and those in which the occurrence of a systematic falsification of the measured value was detected in the recovery test.

Figure 2:
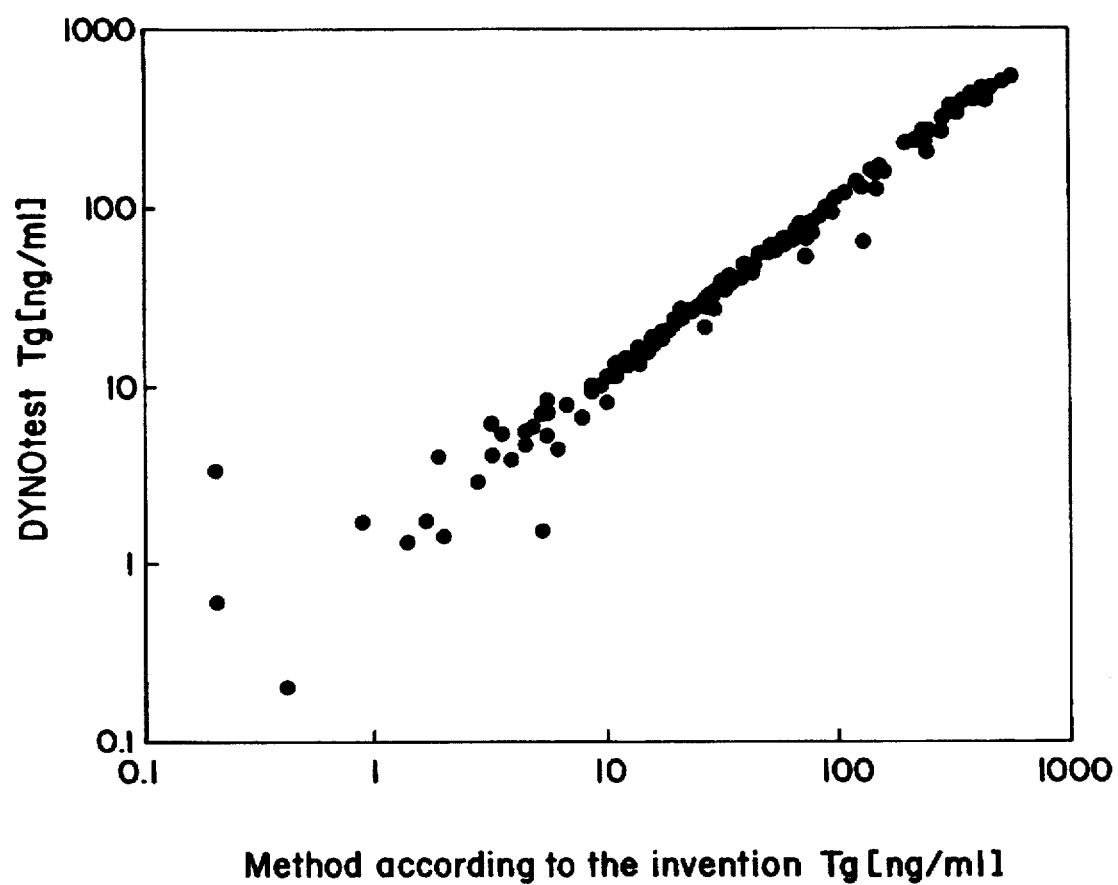
FIG. 2 shows the correlation of the known test with the test according to the invention for patient samples with correct recovery.

FIG. 2 shows that there was an excellent correlation between the results of the known DYNOTEST TG ASSAY and the test according to the invention, the correlation coefficient being 0.99.

Figure 3:
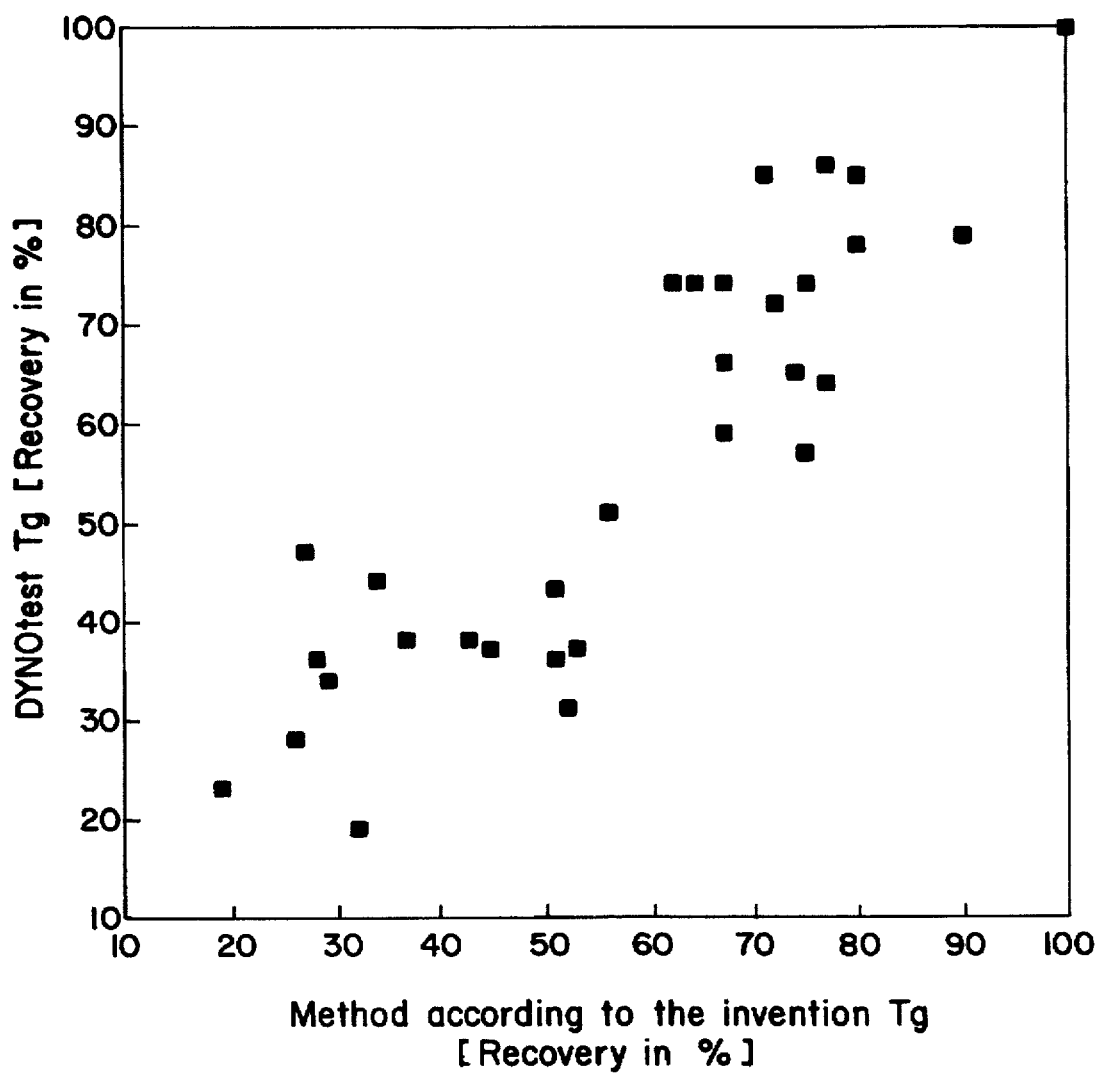
FIG. 3 shows a corresponding correlation for samples in which, on the basis of recovery tests, it had to be assumed that components which falsify the measured value were present in the patient's sample.

FIG. 3 furthermore shows that there was essentially a good correlation between the two tests even in the case of the samples with incorrect recovery (correlation coefficient 0.79), but that many samples which would have been considered to have given acceptable results in the known test on the basis of recovery of more than 70% clearly appear to contain a measurement error in the method according to the invention on the basis of a marked decrease in the measured value for the base signal.

While in the known method the values shown were obtained by means of two measurements per sample, i.e. for the original sample and sample+recovery, corresponding results with the same precision and information content were obtained by a single determination in the method according to the invention.

The method according to the invention thus proves to be a method equivalent to the known method with regard to the accuracy of measurement but furthermore has the advantage that, in the case of measured values which in the known method provide only the information "no or virtually no Tg" (measured values in the region of 0 ng Tg/ml in the Table), it is simultaneously established in the method according to the invention whether the measured value obtained can be correct or whether, on the basis of a detected decrease in the measured base value for the added amount, it was determined in a measurement involving a systematic error.

TABLE 2

| Patient | Method according to the invention [mg Tg/ml] | DYNO TEST TG ASSAY [mg Tg/ml] | Recovery [%] |
| --- | --- | --- | --- |
| 1 | 546 | 555 | 96 |
| 2 | 439 | 482 | 95 |
| 3 | 431 | 475 | 97 |
| 4 | 409 | 476 | 82 |
| 5 | 379 | 420 | 96 |
| 6 | 375 | 437 | 94 |
| 7 | 354 | 415 | 87 |
| 8 | 336 | 402 | 97 |
| 9 | 327 | 377 | 99 |
| 10 | 319 | 354 | 99 |
| 11 | 308 | 371 | 104 |
| 12 | 285 | 324 | 104 |
| 13 | 278 | 269 | 109 |
| 14 | 243 | 209 | 95 |
| 15 | 241 | 278 | 108 |
| 16 | 236 | 238 | 104 |
| 17 | 235 | 276 | 100 |
| 18 | 228 | 244 | 108 |
| 19 | 212 | 244 | 100 |
| 20 | 196 | 235 | 103 |
| 21 | 157 | 158 | 98 |
| 22 | 152 | 172 | 102 |
| 23 | 147 | 127 | 91 |
| 24 | 146 | 165 | 101 |
| 25 | 145 | 156 | 98 |
| 26 | 141 | 161 | 101 |
| 27 | 131 | 63 | 94 |
| 28 | 126 | 130 | 95 |
| 29 | 108 | 121 | 91 |
| 30 | 98 | 112 | 93 |
| 31 | 93 | 93 | 96 |
| 32 | 90 | 95 | 93 |
| 33 | 89 | 98 | 103 |
| 34 | 88 | 95 | 100 |
| 35 | 82 | 88 | 88 |
| 36 | 78 | 81 | 91 |
| 37 | 77 | 71 | 95 |
| 38 | 77 | 83 | 97 |
| 39 | 78 | 66 | 97 |
| 40 | 73 | 53 | 96 |
| 41 | 69 | 80 | 93 |
| 42 | 67 | 75 | 96 |
| 43 | 64 | 65 | 100 |
| 44 | 62 | 66 | 91 |
| 45 | 61 | 67 | 93 |
| 46 | 60 | 66 | 95 |
| 47 | 60 | 66 | 95 |
| 48 | 58 | 65 | 96 |
| 49 | 58 | 62 | 94 |
| 50 | 57 | 64 | 94 |
| 51 | 57 | 63 | 96 |
| 52 | 57 | 61 | 96 |
| 53 | 53 | 58 | 99 |
| 54 | 51 | 60 | 96 |
| 55 | 51 | 60 | 86 |
| 56 | 51 | 57 | 93 |
| 57 | 50 | 56 | 89 |
| 58 | 43 | 42 | 87 |
| 59 | 43 | 48 | 97 |
| 60 | 40 | 47 | 92 |
| 61 | 40 | 44 | 88 |
| 62 | 40 | 42 | 91 |
| 63 | 39 | 40 | 95 |
| 64 | 38 | 39 | 96 |
| 65 | 35 | 60 | 91 |
| 66 | 34 | 37 | 96 |
| 67 | 34 | 40 | 39 |
| 68 | 33 | 36 | 95 |
| 69 | 33 | 36 | 97 |
| 70 | 33 | 34 | 91 |
| 71 | 32 | 37 | 87 |
| 72 | 32 | 35 | 93 |
| 73 | 30 | 33 | 93 |
| 74 | 30 | 26 | 72 |
| 75 | 30 | 33 | 94 |
| 76 | 29 | 32 | 95 |
| 77 | 29 | 31 | 96 |
| 78 | 28 | 31 | 93 |
| 79 | 28 | 31 | 93 |
| 80 | 27 | 29 | 92 |
| 81 | 27 | 28 | 92 |
| 82 | 27 | 27 | 96 |
| 83 | 27 | 21 | 98 |
| 84 | 25 | 27 | 87 |
| 85 | 24 | 26 | 91 |
| 86 | 23 | 26 | 94 |
| 87 | 21 | 23.3 | 91 |
| 88 | 21 | 26 | 96 |
| 89 | 20 | 22 | 97 |
| 90 | 20 | 22 | 89 |
| 91 | 18 | 20 | 92 |
| 92 | 17 | 19 | 89 |
| 93 | 17 | 19 | 95 |
| 94 | 17 | 18 | 97 |
| 95 | 17 | 19 | 97 |
| 96 | 16 | 18 | 89 |
| 97 | 16 | 17 | 94 |
| 98 | 15 | 15 | 97 |
| 99 | 14 | 16 | 90 |
| 100 | 14 | 13 | 94 |
| 101 | 12.3 | 13 | 94 |
| 102 | 11 | 11 | 94 |
| 103 | 10 | 11 | 95 |
| 104 | 10 | 8,2 | 93 |
| 105 | 9,4 | 10 | 99 |
| 106 | 8,7 | 9 | 95 |
| 107 | 8,6 | 9,5 | 95 |
| 108 | 7,8 | 6,6 | 87 |
| 109 | 6,1 | 4,4 | 86 |
| 110 | 5,5 | 7,1 | 97 |
| 111 | 5,4 | 5,3 | 73 |
| 112 | 5,2 | 73 | 93 |
| 113 | 5,2 | 1,5 | 65 |
| 114 | 4,8 | 5,9 | 89 |
| 115 | 4,4 | 5,6 | 91 |
| 116 | 4,4 | 4,7 | 61 |
| 117 | 4,4 | 4,7 | 93 |
| 118 | 3,8 | 3,8 | 91 |
| 119 | 3,2 | 6,2 | 33 |
| 120 | 2,8 | 2,9 | 96 |
| 121 | 2 | 1,4 | 101 |
| 122 | 1.9 | 4 | 89 |
| 123 | 1,4 | 1,3 | 55 |
| 124 | 0,9 | 1,7 | 83 |
| 125 | 0,4 | 0,2 | 85 |
| 126 | 0,2 | 3,4 | 41 |
| 127 | 0,2 | 0,6 | 50 |
| 128 | 0 | 0 | 92 |
| 129 | 1,7 | 1,7 | 88 |
| 130 | 11 | 13 | 91 |
| 131 | 13 | 14 | 95 |
| 132 | 12 | 14 | 92 |
| 133 | 46 | 54 | 98 |
| 134 | 20 | 23 | 86 |
| 135 | 8,6 | 10 | 90 |
| 136 | 12 | 13 | 89 |
| 137 | 14 | 15 | 91 |
| 138 | 6,6 | 7,8 | 88 |
| 139 | 23 | 26 | 86 |
| 140 | 500 | 513 | 95 |
| 141 | 121 | 138 | 96 |

TABLE 2-continued

| Patient | Method according to the invention [mg Tg/ml] | DYNO TEST TG ASSAY [mg Tg/ml] | Recovery [%] |
|---|---|---|---|
| 142 | 367 | 425 | 89 |
| 143 | 429 | 407 | 91 |
| 144 | 0 | 0,9 | 59 |
| 145 | 3,2 | 4 | 61 |
| 146 | 3,5 | 5,4 | 76 |
| 147 | 3,5 | 8,4 | 73 |
| | Measured values < 0 Std. in % | | |
| 148 | 28% | 0 | 36 |
| 149 | 77% | 0 | 86 |
| 150 | 37% | 0 | 38 |
| 151 | 64% | 0 | 74 |
| 152 | 56% | 0 | 51 |
| 153 | 52% | 0,5 | 31 |
| 154 | 27% | 0 | 47 |
| 155 | 32% | 2 | 19 |
| 156 | 19% | 2,8 | 23 |
| 157 | 51% | 3,7 | 43 |
| 158 | 77% | 0 | 64 |
| 159 | 29% | 0 | 34 |
| 160 | 26% | 0 | 28 |
| 161 | 34% | 0 | 44 |
| 162 | 75% | 0,7 | 57 |
| 163 | 67% | 0,4 | 59 |
| 164 | 67% | 0 | 66 |
| 165 | 71% | 0 | 85 |
| 166 | 62% | 0 | 74 |
| 167 | 53% | 0 | 37 |
| 168 | 45% | 0 | 37 |
| 169 | 80% | 0 | 85 |
| 170 | 80% | 0 | 78 |
| 171 | 72% | 0 | 72 |
| 172 | 67% | 0 | 74 |
| 173 | 43% | 0 | 38 |
| 174 | 75% | 0 | 74 |
| 175 | 74% | 0 | 65 |
| 176 | 98% | 0 | 79 |
| 177 | 67% | 0.2 | 66 |
| 178 | 51% | 0 | 36 |
| 179 | 100% | 0 | 100 |

Std. represents the measured value for the zero standard

In the determination of Tg by the method according to the invention using test tubes which contain a predetermined amount of Tg from the outset, it was clear that the advantages of such precoated test tubes can also be utilized in the conventional test with separate recovery by adding to an appropriate kit for the recovery a particular set of test tubes which contains the added amount for the separate recovery measurement as a coating instead of a Tg solution which is to be added to the recovery samples. In this case, too, there are some considerable practical advantages over the conventional method, namely working in the same liquid volumes in the case of determination and recovery measurement, the avoidance of additional sources of error during pipetting of the additional recovery sample and the possibility of an automated determination. By suitable labelling of the tubes for the recovery measurement, for example by a different colouring or clear marking of such tubes, possible sources of error due to confusion of the test tubes can be reliably ruled out.

Test tubes intended for carrying out separate recovery measurements differ from the test tubes which are intended for carrying out the initially described determination method without separate recovery measurement essentially only through a generally larger amount of thyreoglobulin per test tube (CT). While the amount of Tg added per test tube is preferably in the range from 0.1 to 0.5 ng/CT for the initially described method according to the invention, it is about 10 times the amount in the case of tubes for separately carrying out a recovery measurement, the amount particularly preferably being 5 ng/CT. The preparation of the two types of tubes is carried out in an essentially identical manner, apart from the use of different amounts of Tg.

In the measurement of 100 patient sera, in some cases with different dilution, while carrying out an additional separate recovery measurement, on the one hand by the conventional method and on the other hand using test tubes precoated with Tg, outstanding agreement between the results of the measurements was obtained. In the measurement of sera without disturbed recovery, the mean value for the recovery was 94.5% according to the conventional method and 96.2% according to the novel variant of the method using test tubes precoated with Tg. In the measurement of sera with disturbed recovery (49 sera), the correlation coefficient of the two variants of the method was 0.88.

I claim:

1. In a method for the determination of human thyroglobulin in a sample of a biological fluid, said method comprising the steps of placing said sample in a reaction vessel;

reacting said sample with immunoglobulin binding partners for human thyroglobulin;

obtaining a signal representing the amount of thyroglobulin in the sample, and evaluating the obtained signal using standard curves which are prepared with the aid of a series of standard samples containing known amounts of thyroglobulin including a zero standard sample which is thyroglobulin-free;

the improvement wherein a fixed additional amount of thyroglobulin is added to each of (a) the sample on which the measurement is to be made, (b) the standard samples and (c) the zero standard sample, before measurement is made, and the evaluation is carried out in such a way that (i) a signal obtained for the sample which is stronger than the signal obtained for the zero standard is regarded as a positive measured value which is indicative of the presence and amount of thyroglobulin in the sample, while (ii) a signal obtained for the sample and being weaker than the signal obtained for the zero standard sample is regarded as an indication of the presence of components which cause a error in the measured value.

2. The method according to claim 1, wherein the determination of thyroglobulin in the sample, standard samples, and zero standard sample is carried out in a sample vessel which contains the fixed added amount of thyroglobulin as a coating on its internal wall.

3. The method according to claim 2, wherein the vessel is a coated tube or a coated well of a microtitration plate, and further contains an immobilized immunological binding partner for thyroglobulin.

4. The method according to claim 1, wherein the fixed added amount of thyroglobulin is such that, in the measurement, it is in the range of 5 to 10 times the amount of thyroglobulin representing the lower detection limit for thyroglobulin in the special immunological assay method used.

5. The method according to claim 1, wherein the assay method is an immunoassay method wherein two monoclonal antibodies which bind to different epitopes of the thyroglobulin molecule and which are present in excess of the amount necessary for binding all thyroglobulin which may be present in the sample are added to the sample, one of said monoclonal antibodies being labelled or able to be labelled by subsequent reaction with a selective labelling agent.

6. The method according to claim 4, wherein the added fixed amount of human thyroglobulin is in the range of 0.1 to 0.5 ng Tg/CT per 250 µl of the measuring solution and is present in lyophilized form in a coated test tube.

7. The method according to claim 6 wherein the added fixed amount of thyroglobulin is present in the amount of 0.3 ng Tg/CT.

8. A kit for the determination of human thyroglobulin according to the method of any of claims 1-7, which in addition to the conventional kit components comprising tracer solution, standard solutions, zero standard and washing liquid, further comprises test tubes which, in addition to an immobilized immunological binding partner for human thyroglobulin, contain a fixed amount of thyroglobulin.

9. The kit according to claim 8, wherein the fixed amount of thyroglobulin is present in lyophilized form as a coating on the internal wall of the test tube.

10. A test tube for the quantitative determination of human thyroglobulin in a sample of a biological fluid by a determination method which uses test tubes, on the walls of which antibodies for binding the thyroglobulin to be determined in the sample are immobilized, wherein the walls of said test tubes are additionally coated with a fixed amount of thyroglobulin.

11. The test tube according to claim 10, wherein the fixed amount of thyroglobulin is applied as a coating in a water-soluble matrix.

12. The test tube according to claim 10 or 11, wherein the fixed amount of thyroglobulin per test tube is in the range from 0.1 to 7 ng Tg/CT.

* * * * *